US007838050B2

(12) United States Patent
Randolph et al.

(10) Patent No.: US 7,838,050 B2
(45) Date of Patent: *Nov. 23, 2010

(54) CYTOKINE MODULATORS AND RELATED METHOD OF USE

(75) Inventors: Russell K. Randolph, Anaheim, CA (US); Haeri Roh-Schmidt, Stockton, CA (US); Mary A. Murray, Irvine, CA (US); Aaron W. Crawford, Los Angeles, CA (US); Kevin W. Gellenbeck, Poway, CA (US); Donald J. Pusateri, Hemet, CA (US)

(73) Assignee: Access Business Group International LLC, Ada, MI (US)

( * ) Notice: Subject to any disclaimer, the term of this patent is extended or adjusted under 35 U.S.C. 154(b) by 365 days.

This patent is subject to a terminal disclaimer.

(21) Appl. No.: 10/938,093

(22) Filed: Sep. 10, 2004

(65) Prior Publication Data

US 2005/0058728 A1 Mar. 17, 2005

Related U.S. Application Data

(60) Provisional application No. 60/502,755, filed on Sep. 12, 2003.

(51) Int. Cl.
*A61K 36/45* (2006.01)
*A61K 36/73* (2006.01)
*A61K 36/906* (2006.01)

(52) U.S. Cl. .................. 424/732; 424/765; 424/756; 514/885

(58) Field of Classification Search .............. 514/886, 514/885; 424/777, 732, 765, 756
See application file for complete search history.

(56) References Cited

U.S. PATENT DOCUMENTS

| 74,147 A | 2/1868 | Rosbrugh |
|---|---|---|
| 4,110,483 A * | 8/1978 | Bishov |
| 4,839,172 A | 6/1989 | Morishige |
| 5,165,932 A | 11/1992 | Horvath |
| 5,466,451 A | 11/1995 | Beuscher et al. |
| 5,527,533 A | 6/1996 | Tso et al. |
| 5,540,931 A | 7/1996 | Hewitt et al. |
| 5,595,743 A | 1/1997 | Wu |
| 5,683,698 A | 11/1997 | Chavali et al. |
| 5,714,150 A | 2/1998 | Nachman |
| 5,854,291 A | 12/1998 | Laughlin et al. |
| 5,916,565 A | 6/1999 | Rose et al. |
| 6,022,901 A | 2/2000 | Goodman |
| 6,024,960 A | 2/2000 | Kharazmi et al. |
| 6,024,998 A | 2/2000 | Kreuter et al. |
| 6,103,218 A | 8/2000 | Brucker et al. |
| 6,146,636 A | 11/2000 | Breton et al. |
| 6,211,247 B1 | 4/2001 | Goodman |
| 6,231,866 B1 | 5/2001 | Mann |
| 6,238,675 B1 | 5/2001 | Pero |
| 6,264,995 B1 | 7/2001 | Newmark et al. |
| 6,274,176 B1 | 8/2001 | Tomer et al. |
| 6,333,056 B1 | 12/2001 | Robinson |
| 6,344,220 B1 | 2/2002 | Rose et al. |
| 6,387,416 B1 | 5/2002 | Newmark et al. |
| 6,391,310 B1 | 5/2002 | Empie et al. |
| 6,410,062 B1 | 6/2002 | Callaghan et al. |
| 6,414,037 B1 | 7/2002 | Pezzuto et al. |
| 6,464,982 B1 | 10/2002 | Lam |
| 6,468,541 B2 | 10/2002 | Lam |
| 6,479,080 B2 | 11/2002 | Bombardelli et al. |
| 6,482,432 B2 | 11/2002 | Wang |
| 6,485,752 B1 | 11/2002 | Rein |
| 6,492,429 B1 | 12/2002 | Graus et al. |

(Continued)

FOREIGN PATENT DOCUMENTS

| CA | 2245123 | 3/1999 |
|---|---|---|
| CA | 2339221 | 12/2000 |
| CA | 2473698 | 7/2003 |
| DE | 101 53 949 A1 | 8/2002 |
| HU | 64860 | 3/1994 |
| HU | 65923 | 7/1994 |
| JP | 7099924 | 4/1995 |
| JP | 7300421 | 11/1995 |
| RU | 2053265 C1 * | 1/1996 |
| SU | 1697820 A1 * | 12/1991 |

(Continued)

OTHER PUBLICATIONS

Bertelli, A. A. et al. International J of Immunotherapy, 2002; 18(3-4): 83-86. Resveratrol prevents interleukin release from isolated monocytes.*

(Continued)

*Primary Examiner*—Michele Flood
(74) *Attorney, Agent, or Firm*—Brinks Hofer Gilson & Lione; G. Peter Nichols

(57) ABSTRACT

A composition for modulating cytokines to regulate an inflammatory or immunomodulatory response. The composition can include at least one of rosehips, blueberry, blackberry, elderberry, cranberry, rosemary, clove, feverfew, nettle root, artichoke, reishi mushroom, olive extract, green tea extract, grape seed extract, resveratrol, *Aframomum melegueta, boswellia serrata* extract, *boswellia forte*, ipriflavone, tocotrienols, evening primrose oil, INM-176, borage oil, krill oil, at least one type of xanthophyll (e.g., astaxanthin), green coffee extract and ferulic acid. Specifically, a composition of the invention can include: rosehips and at least one of blackberry, blueberry, elderberry, and optionally krill oil; or rosehips, resveratrol and at least one of *Aframomum melegueta* and astaxanthin. Based on the cytokine modulation and cytokine response inhibition of the composition, it can be used to regulate an immunomodulatory and/or inflammatory response, and subsequently treat diseases and/or abnormal conditions associated with inflammatory response, for example, cardiovascular conditions, arthritis, osteoporosis and Alzheimer's disease.

7 Claims, 2 Drawing Sheets

U.S. PATENT DOCUMENTS

| | | |
|---|---|---|
| 6,500,450 B1 | 12/2002 | Hendrix |
| 6,572,882 B1 | 6/2003 | Vercauteren et al. |
| 6,579,543 B1 | 6/2003 | McClung |
| 6,582,736 B2 | 6/2003 | Quezada |
| 6,586,020 B1 | 7/2003 | Breton et al. |
| 6,605,296 B1 | 8/2003 | Stuckler |
| 6,638,542 B2 | 10/2003 | Nieuwenhuizen et al. |
| 6,638,545 B1 | 10/2003 | Rombi |
| 6,642,277 B1 | 11/2003 | Howard et al. |
| 6,656,925 B2 | 12/2003 | Petrus |
| 6,716,883 B1 | 4/2004 | Casper et al. |
| 6,753,019 B1 | 6/2004 | Lang et al. |
| 2001/0012525 A1 | 8/2001 | Mann |
| 2001/0021400 A1 | 9/2001 | Bombardelli et al. |
| 2001/0039296 A1 | 11/2001 | Bagchi et al. |
| 2001/0044411 A1 | 11/2001 | Gelber et al. |
| 2001/0056071 A1 | 12/2001 | Pelliccia et al. |
| 2002/0004077 A1 | 1/2002 | Cuomo et al. |
| 2002/0054924 A1 | 5/2002 | Leahy et al. |
| 2002/0064568 A1 | 5/2002 | Rose et al. |
| 2002/0102315 A1 | 8/2002 | Leko |
| 2002/0119173 A1 | 8/2002 | Lin et al. |
| 2002/0119952 A1 | 8/2002 | Petrus |
| 2002/0127243 A1 | 9/2002 | Sun |
| 2002/0136788 A1 | 9/2002 | Quezada |
| 2002/0141987 A1 | 10/2002 | Bjarnason |
| 2002/0146472 A1 | 10/2002 | Chen et al. |
| 2002/0168429 A1 | 11/2002 | Mann |
| 2002/0168430 A1 | 11/2002 | Heeg et al. |
| 2002/0173472 A1 | 11/2002 | Pezzuto et al. |
| 2002/0182260 A1 | 12/2002 | Mak et al. |
| 2003/0017217 A1 | 1/2003 | Quintanilla Almagro |
| 2003/0044474 A1 | 3/2003 | Tao et al. |
| 2003/0049335 A1 | 3/2003 | Stier et al. |
| 2003/0077343 A1 | 4/2003 | Martin et al. |
| 2003/0078304 A1 | 4/2003 | Andersson et al. |
| 2003/0086986 A1 | 5/2003 | Bruijn et al. |
| 2003/0108627 A1 | 6/2003 | Selzer et al. |
| 2003/0139350 A1* | 7/2003 | Larsen et al. |
| 2003/0143292 A1 | 7/2003 | Cho |
| 2003/0161897 A1 | 8/2003 | Shanbrom |
| 2003/0165589 A1 | 9/2003 | Cals-Grieson |
| 2003/0190381 A1 | 10/2003 | Bland et al. |
| 2003/0194456 A1 | 10/2003 | Arora et al. |
| 2003/0203054 A1 | 10/2003 | Selzer et al. |
| 2004/0014721 A1 | 1/2004 | Hensley et al. |
| 2004/0022818 A1 | 2/2004 | Cho et al. |
| 2004/0037903 A1 | 2/2004 | Lemmo et al. |
| 2004/0086579 A1 | 5/2004 | Higgins et al. |
| 2004/0109905 A1 | 6/2004 | Bagchi |
| 2004/0121024 A1 | 6/2004 | Gorsek |
| 2004/0151761 A1 | 8/2004 | Chew et al. |
| 2004/0162338 A1 | 8/2004 | Schmitz |
| 2004/0247706 A1 | 12/2004 | Roberts |
| 2005/0031573 A1 | 2/2005 | Cho et al. |
| 2005/0037095 A1 | 2/2005 | Bailey et al. |
| 2005/0058728 A1 | 3/2005 | Randolph et al. |

FOREIGN PATENT DOCUMENTS

| | | |
|---|---|---|
| WO | WO 98/37874 | 9/1998 |
| WO | WO 98/45241 | 10/1998 |
| WO | WO 99/11251 | 3/1999 |
| WO | WO 99/53934 A1 | 10/1999 |
| WO | WO 99/59561 | 11/1999 |
| WO | WO 01/95727 | 12/2001 |
| WO | WO 2005/025586 A1 | 3/2005 |
| WO | WO 2005/027716 A2 | 3/2005 |
| WO | WO 2005/112965 A2 | 12/2005 |

OTHER PUBLICATIONS

Umukoro, S. et al. Nig. Ol. J. Hosp. Med., 2001; 11(1-4): 33-35. Effects of *Aframomum meleguta* seed extract on thermal pain and carrageenin-induced oedema.* http://en.wikipedia.org/wiki/Blueberry. "Blueberry"pp. 1-6. Downloaded Jan. 24, 2007.*

Alternative Medicine Review (2005); 10(1): 51-55. Monograph: *Sambucus nigra* (Elderberrry).*

Bertelli, A. A. et al. International J of Immunotherapy, 2002; 18(3-4): 83-86. Resveratrol prevents interleukin release from isolated monocytes.*

Tallarida, RJ. British Journal of Pharmacology (2002); 135: 1589-1590. Commentary on neostigmine interation with non steroidal anti-inflammatory drugs by Miranda et al.*

Marquina, M et al. Fitoperia (2002). 73(7-8): 727-729. Hyaluronidase inhibitory activity from the fruit of blueberry (*Rubus fruticosus* B.).*

Schulze-Tanzil, G., et al, Effects of the antirheumatic remedy hox alpha—a new stinging nettle leaf extract—on matrix metalloproteinases in human chondrocytes in vitro, Histol Histopathol. Apr. 2002; 17(2); 477-85 (abstract only).

Piela-Smith TH, et al, Feverfew extracts and the sesquiterpene lactone parthenolide inhibit intercellular adhesion molecule-1 expression in human synovial fibroblasts, Cell Immunol., May 1, 2001; 209(2); 89-96 (abstract only).

Yesilada, E., et al, Inhibitory effects of Turkish folk remedies on inflammatory cytokines: interleukin-1 alpha, interleukin-1 beta and tumor necrosis factor alpha, J. Ethnopharmacol, Sep. 1997; 58(1); 59-73 (abstract only).

Hwang, D., et al, Inhibition of the expression of inducible cyclooxygenase and proinflammatory cytokines by sesquiterpene lactones in macrophages correlates with the inhibition of MAP kinases, Biochem Biophys Res Commun, Sep 24, 1996; 226(3); 810-8 (abstract only).

Teucher, T., et al, Cytokine secretion in whole blood of healthy subjects following oral administration of *Urtica dioica* L. plant extract, Arzneimittelforschung, Sep. 1996; 46(9); 906-10 (abstract only).

Le Moal, MA, et al, Urtica dioica agglutinin, a new mitogen for murine T lymphocytes: unaltered interleukin-1 production but late interleukin 2-mediated proliferation, Cell Immunol., Aug. 1988; 115(1); 24-35 (abstract only).

O'Neill, LA, et al, Extracts of feverfew inhibit mitogen-induced human peripheral blood mononuclear cell proliferation and cytokine mediated responses: a cytotoxic effect; Br J Clin Pharmacol., Jan. 1987; 23(1); 81-3 (abstract only).

Ebringer, A, et al, Rheumatoid arthritis: proposal for the use of anti-microbial therapy in early cases; Scand J Rheumatol., 2003; 32(1); 2-11 (abstract only).

Rossi, A., et al, Protective effects of anthocyanins from blackberry in a rat model of acute lung inflammation, Free Radic Res., Aug. 2003; 37(8); 891-900 (abstract only).

Roy, S., et al, Anti-angiogenic property of edible berries, Free Radic Res., Sep. 2002, 36(9); 1023-31 (abstract only).

Youdim, KA, et al., Potential role of dietary flavonoids in reducing microvascular endothelium vulnerability to oxidative and inflammatory insults (small star, filled), J Nutr Biochem., May 2002; 13(5); 282-288 (abstract only).

Bertelli, AA, et al, Oxidative stress and inflammatory reaction modulation by white wine, Ann NY Acad Sci., May 2002, 957; 295-301 (abstract only).

Bertelli, A, et al, Effect of some white wine phenols in preventing inflammatory cytokine release, Drugs Exp Clin Res., 2002, 28(1); 11-5 (abstract only).

Wallace, FA, et al, Activation state alters the effect of dietary fatty acids on pro-inflammatory mediator production by murine macrophages, Cytokine, Sep. 2000; 12(9); 1374-9 (abstract only).

Sadeghi, S, et al, Dietary lipids modify the cytokine response to bacterial lipopolysaccharide in mice, Immunology, Mar. 1999; 96(3); 404-10 (abstract only).

De Pablo, MA, et al, The effect of dietary fatty acid manipulation on phagocytic activity and cytokine production by peritoneal cells from Balb/c mice, J Nutri Sci Vitaminol (Tokyo), Feb. 1998; 44(1); 57-67 (abstract only).

Tappia, PS, et al, The relationship between altered membrane composition, eicosanoids and TNF-induced IL1 and IL6 production in macrophages of rats fed fats of different unsaturated fatty acid composition, Mol Cell Biochem., Dec. 20, 1996; 165(2); 135-43 (abstract only).

Tappia, PS, et al, Complex modulation of cytokine induction by endotoxin and tumour necrosis factor from peritoneal macrophages of rats by diets containing fats of different saturated, monounsaturated and polyunsaturated fatty acid composition, Clin Sci (Lond)., Aug. 1994; 87(2); 173-8 (abstract only).

Kremer, JM, et al, Dietary fish oil and olive oil supplementation in patients with rheumatoid arthritis. Clinical and immunologic effects., Arthritis Rheum., Jun. 1990; 33(6); 810-20 (abstract only).

Martin, AR, et al, Resveratrol, a polyphenol found in grapes, suppresses oxidative damage and stimulates apoptosis during early colonic inflammation in rats, Biochem Pharmacol., Apr. 1, 2004; 67(7); 1399-410 (abstract only).

Culpitt, SV, et al, Inhibition by red wine extract, resveratrol, of cytokine release by alveolar macrophages in COPD, Thorax., Nov. 2003; 58(11); 942-6 (abstract only).

Estrov, Z, et al, Resveratrol blocks interleukin-1beta-induced activation of the nuclear transcription factor NF-kappaB, inhibits proliferation, causes S-phase arrest, and induces apoptosis of acute myeloid leukemia cells, Blood, Aug. 1, 2003; 102(3); 987-95, Epub Apr. 10, 2003 (abstract only).

Feng, YH, et al, Effects of resveratrol and ethanol on production of pro-inflammatory factors from endotoxin activated murine macrophages, Acta Pharmacol Sin., Nov. 2002; 23(11); 1002-6 (abstract only).

Neptune Technologies and Bioresources Scientific Report, URL: http://www.fda.gov/ohrms/dockets/dockets/95s0316/95s-0316-rpt0131-08-Appendix-F-vol95.pdf.

Preclinical Study of Immunobioactive Properties of Topix Preparation Isolated from Tubers of Jerusalem Artichoke, URL: http//www.nioch.nsc.ru/icnpas98/pdf/posters1/55.pdf.

Life Extensions: Polymyalgia Rheumatica, URL: http://www.lef.org/protocols/prtcls-txt/t-prtcl-116.html.

Casper, et al, Resveratrol Has Antagonist Activity on the Aryl Hydrocarbon Receptor: Implications for Prevention of Dioxin Toxicity, Mol Pharmacol., Oct. ; 56(4); 784-790.

Guerin, Martin, et al, Haematococcus astaxanthin: health and nutritional applications, Mera Pharmaceuticals, Inc., 2002; 1-19.

Blue Goo and the Healthy Heart, URL: http://www.mercola.com/2000/sep/3/microalgae.htm.

Kurashige, Michi, et al, Inhibition of Oxidative Injury of Biological Membranes by Attaxanthin, Physiol Chem Phys & Med NMR, 1990; 22; 27-38.

Estruch, Ramon, et al, Different effects of red wine and gin consumption on inflammatory biomarkers of atherosclerosis: a prospective randomized crossover trial Effects of wine on inflammatory markers, Atherosclerosis, 2004; 175; 117-123.

Popova, NV, et al, Carotenoids of the fruit of Capsicum annuum, Farm Zh (Kiev), 1985; 6; 50-4, No translation of foreign languge document Astaxanthin and Inflammatory Cytokines, Teltech Research Services, Aug. 11, 2004; 1-17.

*Aframomum melegueta*, Teltech Research Services, Aug. 13, 2004; 1-13.

Yesilada E et al, Inhibitory Effects of Turkish Folk Remedies on Inflammatory Cytokines: Interleukin-1Alpha, Interleukin-1Beta and Tumour Necrosis Factor Alpha, Journal of Ethnopharmacology, Elsevier Scientific Publishers Ltd, IE, vol. 58, 1997, pp. 59-73.

Wang J et al, Inhibitory effects of anthocyanins and other phenolic compounds on nitric oxide production in LPS/IFM-gamma-activated RAW 264.7 macrophages, Journal of Agricultural and Food Chemistry, vol. 50, No. 4, Feb. 13, 2002, pp. 850-857.

Youdim Kuresh A et al, Potential role of dietary flavonoids in reducing microvascular endothelium vulnerability to oxidative and inflammatory insults, Journal of Nutritional Biochemistry, vol. 13, No. 5, May 2002, pp. 282-288.

Database Biosis Online! Biosciences Information Service, Philadelphia, PA, US; 2003; Galli R L et al, Amelioration of LPS-induced indices of inflammation by blueberry extract in cells, Database accession No. PREV200400203086, & Society for Neuroscience Abstract Viewer and Itinery Planner, vol. 2003, 2003, pp Abstract No. 638.12, URL-http://sf, 33rd Annual Meeting of the Society of Neuroscience: New Orleans, LA, USA; Nov. 8-12, 2003.

Frautschy S A et al, Prevention of Abeta amyloid peptide infusion-induced behavioral deficits neuroinflammation and neurodegeneration by dietary anti-inflammatory/antioxidant supplements, Society for Neuroscience Abstracts, vol. 26, No. 1-2, 2000; pp Abstract No. -680.8 and 30th Annual Meeting of the Society of Neuroscience; New Orleans, LA, USA; Nov. 4-9, 2000.

Barak Vivian et al, The effect of Sambucol, a black elderberry-based, natural product, on the production of human cytokines: I. Inflammatory cytokines, European Cytokine Network, vol. 12, No. 2, Apr. 2001, pp. 290-296.

Rossi Antonietta et al, Protective effects of anthocyanins from blackberry in a rat model of acute lung inflammation, Free Radical Research vol. 37, No. 8, Aug. 2003, pp. 891-900.

Barak Vivian et al, The effect of herbal remedies on the production of human inflammatory and anti-inflammatory cytokines, The Israel Medical Assoc. Journal, IMAJ, Nov. 2002, vol. 4, No. 11 Suppl, Nov. 2002, pp. 919-922.

Manna S K et al, Resveratrol suppresses TNF-induced activation of nuclear transcription factors NF-kappa B, activator protein-1, and apoptosis: potential role of reactive oxygen intermediates and lipid peroxidation, Journal of Immunology (Baltimore, MD: 1950) vol. 164, No. 12, Jun. 15, 2000, pp. 6509-6519.

Gao X et al, Immunomodulatory activity of resveratrol: suppression of lymphocyte proliferation, development of cell-mediated cytotoxicity, and cytokine production, Biochemical Pharmacology, Pergamon, Oxford, GB, vol. 62, Nov. 1, 2001, pp. 1299-1308.

Wadsworth Teri L et al, Effects of the wine polyphenolics quercetin and resveratrol on pro-inflammatory cytokine expression in RAW 264.7 macrophages, Biochemical Pharmacology, vol. 57, No. 8, Apr. 15, 1999, pp. 941-949.

Guerin M et al, Haematococcus astaxanthin: applications for human health and nutrition, Trends in Biotechnology, Elsevier Publications, Cambridge, GB, vol. 21, No. 5, May 2003, pp. 210-216.

Anonymous, Symptom: H(097) Description: orchitis, testicles inflammation, Internet Article, 'Online!, retrieved from the Internet: <URL:http://www.metafro.be/prelude/view_symptom?si=H(097)> retrieved on Jan. 7, 2005! Fernandez de la Pradilla, C.: Des plantes qui nous ont gueris, 1981 Burkina Faso.

Popova, NV et al, "Carotenoids of the fruit of *Capsicum annuum*", *Farm. Zh. (Kiev)*, vol. 6, pp. 50-54, 1985 (and English abstract).

O'Neill, LA et al., "Extracts of feverfew inhibit mitogen-induced human peripheral blood mononuclear cell proliferation and cytokine mediated responses: a cytotoxic effect", *Br J Clin Pharmcol*, 23(1): 81-3, Jan. 1987 (abstract only).

Le Moal, MA et al., "Urtica dioica agglutinin, a new mitogen for murine T lymphocytes: unaltered interleukin-1 production but late interleukin 2-mediated proliferation", *Cell Immunol*, 115(1): 24-35, Aug. 1988 (abstract only).

Kurashige, Michi et al., "Inhibition of Oxidative Injury of Biological Membranes by Astaxanthin", *Physiol Chem Phys & Med NMR*, 22: 27-38, 1990.

Kremer, JM et al., "Dietary fish oil and olive oil supplementation in patients with rheumatoid arthritis. Clinical and immunologic effects.", *Arthritis Rheum.*, 33(6): 810-20, Jun. 1990 (abstract only).

Tappia, PS. et al., "Complex modulation of cytokine induction by endotoxin and tumour necrosis factor from peritoneal macrophages of rats by diet containing fats of different saturated, monosaturated and polyunsaturated fatty acid composition", *Clin Sci (Lond).*, 87(2): 173-8, Aug. 1994 (abstract only).

Hwang, D. et al., "Inhibition of the expression of inducible cyclooxygenase and proinflammatory cytokines by sesquiterpene lactones in macrophages correlates with the inhibition of MAP kinases", *Biochem Biophys Res Commun*, 226(3); 810-8, Sep. 24, 1996 (abstract only).

Teucher, T. et al., "Cytokine secretion in whole blood of healthy subjects following oral administration of *Urtica dioica* L. plant extract", *Arzneimittelforschung*, 46(9): 906-10, Sep. 1996 (abstract only).

Tappia, PS et al., "The relationship between altered membrane composition, eicosanoids and TNF-induced IL1 and IL6 production in macrophages of rats fed fats of different unsaturated fatty acid composition", *Mol Cell Biochem.*, 165(2): 135-43, Dec. 20, 1996 (abstract only).

Yesilada, Erdem et al., "Inhibitory effects of Turkish folk remedies on inflammatory cytokines: interleukin-1α, interleukin-1β and tumor necrosis factor α", *Journal of Ethnopharmacology*, 58: 59-73, 1997.

Zelenkov, V.N. et al., "Preclinical Study of Immunoactive Properties of Topix Preparation Isolated from Tubers of Jerusalem Artichoke" *Novosibirsk Institute of Organic Chemistry*, Abstracts of Posters, obtained at Internet address <http://www.nioch.nsc.ru/icnpas98/pdf/posters1/55.pdf>, 1 page, 1998.

de Pablo, MA et al., "The effect of dietary fatty acid manipulation on phagocytic activity and cytokine production by peritoneal cells from Balb/c mice", *J Nutri Sci Vitaminol* (Tokyo), 44(1): 57-67, Feb. 1998 (abstract only).

Wadsworth, Teri L. et al., "Effects of the Wine Polyphenolics Quercetin and Resveratrol on Pro-inflammatory Cytokine Expression in RAW 264.7 Macrophages", *Biochemical Pharmacology*, vol. 57, pp. 941-949, 1999.

Sadeghi, S et al., "Dietary lipids modify the cytokine response to bacterial lipopolysaccharide in mice", *Immunology*, 96(3): 404-10, Mar. 1999 (abstract only).

Casper et al., "Resveratol Has Antagonist Activity on the Aryl Hydrocarbon Receptor: Implications for Prevention of Dioxin Toxicity", *Mol Pharmacol.*, 56(4): 784-790, Oct. 1999.

Manna, Sunil K et al., "Resveratrol Suppresses TNF-Induced Activation of Nuclear Transcription Factors NF-κB, Activator Protein-1, and Apoptosis: Potential Role of Reactive Oxygen Intermediates and Lipid Peroxidation", *Journal of Immunology*, vol. 164, No. 12, pp. 6509-6519, Jun. 15, 2000.

Website of Dr. Joseph Mercola, "Blue Goo and the Healthy Heart", obtained at Internet address <http://www.mercola.com/2000/sep/3/microalgae.htm>, 4 pages, Aug. 2000.

Wallace, FA et al., "Activation state alters the effect of dietary fatty acids on pro-inflammatory mediator production by murine macrophages", *Cytokine*, 12(9): 1374-9, Sep. 2000 (abstract only).

Frautschy, S.A. et al., "Prevention of Aβ Amyloid Peptide Infusion-Induced Behavioral Deficits Neuroinflammation and Neurodegeneration by Dietary Anti-Inflammatory/Antioxidant Supplements", *Society for Neuroscience Abstracts*, vol. 26, No. 1-2, Abstract No. 680.8, 1 page, and *30th Annual Meeting of the Society of Neuroscience*, New Orleans, LA, USA, Nov. 4-9, 2000 (abstract only).

Gao, Xiaohua et al., "Immunomodulatory activity of resveratrol: suppression of lymphocyte proliferation, development of cell-mediated cytotoxicity, and cytokine production", *Biochemical Pharmacology*, 62, 1299-1308, 2001.

Piela-Smith TH et al., "Feverfew extracts and the sesquiterpene lactone parthenolide inhibit intercellular adhesion molecule-1 expression in human synovial fibroblasts", *Cell Immunol.*, 209(2): 89-96, May 1, 2001 (abstract only).

Barak, Vivian et al., "The effect of Sambucol, a black elderberry-based, natural product, on the production of human cytokines: I. Inflammatory cytokines", *Eur. Cytokine Netw.*, vol. 12, No. 2, pp. 290-296, Jun. 2001.

Bertelli, A et al., "Effect of some white wine phenols in preventing inflammatory cytokine release", *Drugs Exp Clin Res.*, 28(1): 11-5, 2002 (abstract only).

Guerin, Martin et al., "*Haematococcus astaxanthin*: health and nutritional applications", *Mera Pharmaceuticals, Inc.*, pp. 1-19, 2002.

Wang, J. et al., "Inhibitory Effects of Anthocyanins and Other Phenolic Compounds on Nitric Oxide Production in LPS/IFN-γ-Activated RAW 264.7 Macrophages", *J. Agric.Food Chem.*, 50, 850-857, 2002.

Schulze-Tanzil, G. et al., "Effects on the antirheumatic remedy hox alpha—a new stinging nettle leaf extract—on matrix metalloproteinases in human chondrocytes in vitro", *Histol Histopathol.*, 17(2): 477-85, Apr. 2002 (abstract only).

Neptune Technologies and Bioresources, "Scientific Report", obtained at Internet address <http://www.fda.gov/ohrms/dockets/dockets/95s0316/95s-0316-rpt0131-08-Appendix-F-vol95.pdf>, 15 pages, Apr. 17, 2002.

Bertelli, AA et al., "Oxidative stress and inflammatory reaction modulation by white wine", *Ann NY Acad Sci.*, 957: 295-301, May 2002 (abstract only).

Youdim, KA et al., "Potential role of dietary flavonoids in reducing microvascular endothelium vulnerability to oxidative and inflammatory insults", *J Nutr Biochem.*, 13(5): pp. 282-288, May 2002.

Roy, S. et al., "Anti-angiogenic property of edible berries", *Free Radic Res.*, 36(9): 1023-31, Sep. 2002 (abstract only).

Barka, Vivian et al., "The Effect of Herbal Remedies on the Production of Human Inflammatory and Anti-inflammatory Cytokines", *The Israel Medical Association Journal (IMAJ)*, vol. 4, No. 11, Supplement, pp. 919-922, Nov. 2002.

Feng, YH et al., "Effects of resveratrol and ethanol on production of pro-inflammatory factors from endotoxin activated murine macrophages", *Acta Pharmacol Sin.*, 23(11): 1002-6, Nov. 2002 (abstract only).

Ebringer, A et al., "Rheumatoid arthritis: proposal for the use of anti-microbial therapy in early cases", *Scand J. Rheumatol.*, 32(1): 2-11, 2003 (abstract only).

Guerin, Martin et al., "Haematococcus astaxanthin: applications for human health and nutrition", *Trends in Biotechnology*, vol. 21, No. 5, pp. 210-216, May 2003.

Website of Life Extensions Magazine, "Life Extensions: Polymyalgia Rheumatica", obtained at Internet address <http://www.lef.org/protocols/prtcls-txt/t-prtcl-116.html>, 11 pages, Jun. 2003.

Estrov, Z et al., "Resveratrol blocks interleukin-1beta-induced activation of the nuclear transcription factor NF-kappaB, inhibits proliferation, causes S-phase arrest, and induces apoptosis of acute myeloid leukemia cells", *Blood*, 102(3): 987-95, Aug. 1, 2003, Epub Apr. 10, 2003 (abstract only).

Rossi, A. et al., "Protective effects of anthocyanins from blackberry in a rat model of acute lung inflammation", *Free Radic Res.*, 37(8): 891-900, Aug. 2003.

Culpitt, SV et al., "Inhibition by red wine extract, resveratrol, of cytokine release by alveolar macrophages in COPD", *Thorax.*, 58(11): 942-6, Nov. 2003 (abstract only).

Galli, RL et al., "Amelioration of LPS-induced indices of inflammation by blueberry extract in cells", *Society for Neuroscience Abstract Viewer and Itinerary Planner*, vol. 2003, Abstract No. 638.12, 2003, and *33rd Annual Meeting of the Society of Neuroscience*, New Orleans, LA, USA, Nov. 8-12, 2003, and *Database Biosis Online! Biosciences Information Service*, Philadelphia, PA, USA, 2 pages, 2003 (abstract only).

Martin, AR et al., "Resveratrol, a polyphenol found in grapes, suppresses oxidative damage and stimulates apoptosis during early colonic inflammation in rats", *Biochem Pharmacol*, 67(7); 1399-410, Apr. 1, 2004 (abstract only).

Estruch, Ramon et al., "Different effects of red wine and gin consumption on inflammatory biomarkers of atherosclerosis: a prospective randomized crossover trial effects of wine on inflammatory markers", *Atherosclerosis*, 175: 117-123, 2004.

Teltech Research Services, "Astaxanthin and Inflammatory Cytokines", *Teltech Research Services*, pp. 1-17, Aug. 11, 2004.

Teltech Research Services, "*Aframomum melgueta*", *Teltech Research Services*, pp. 1-13, Aug. 13, 2004.

Anonymous Internet Article, "Symptom: H(097) Description: orchitis, testicles inflammation", *Online!*, obtained at Internet address <http://www.metafro.be/prelude/view_symptom?si=H(097)>, on Jan. 7, 2005, and Fernandez de la Pradilla, C., "Des plantes qui nous ont gueris", Burkina Faso, Tome 1, p. 208, 1981.

International Search Report in PCT Application No. PCT/US2006/032847, dated Jan. 29, 2007, 11 pages.

Written Opinion in PCT Application No. PCT/US2006/032847, dated Jan. 29, 2007, 13 pages.

Anonymous, *Healtheries 100 Years*, "Wildberry with Blackberry, Raspberry & Blueberry Tea", Date unknown, obtained at the internet address <http://www.healtheries.co.nz/page.php?id=25&prod=1088> on Jan. 5, 2007, 2 pages.

Anonymous, TeaNewEngland.com, "Blueberry Box", Date unknown, obtained at the internet address <http://www.teanewengland.com/catalog/product_info.php?products_id=28&osCsid=> on Jan. 12, 2007, 1 page.

Anonymous, ClinicalTrials.gov, "Study to Evaluate the Effect of Botanical Dietary Supplements on Inflammation in Healthy People", Date unknown, obtained at the Internet address <http://www.clinicaltrials.gov/show/NCT00303238> on Jan. 10, 2007, 4 pages.

Dybas, Cheryl Lyn, WashingtonPost.com, "Gorilla Staple Adds Spice to New Drugs", Nov. 27, 2006, obtained at the internet address <http://www.washingtonpost.com/wp-dyn/content/article/2006/11/26/AR2006112600730_pf.html> on Jan. 10, 2007, 2 pages.

Liu, B-L et al., "Vaticanol (B, C and G), [alpha]-viniferin, and hopeaphenol inhibit mediator release from bone marrow-derived mouse mast cells in vitro", *Chinese Journal of Natural Medicines*, vol. 2, No. 3, 2004, pp. 176-183, Abstract only, 2 pages.

Umukoro, S., "Effects of *Aframomum meleguta* Seed Extract on Thermal Pain and Carrageenin-Induced Oedema", *Nigerian Quarterly Journal of Hospital Medicine*, vol. 11, No. 1-4, Dec. 2001, pp. 33-35.

* cited by examiner

US 7,838,050 B2

CYTOKINE MODULATORS AND RELATED METHOD OF USE

This application claims benefit of U.S. Provisional Application 60/502,755, filed Sep. 12, 2003, which is hereby incorporated by reference.

BACKGROUND OF THE INVENTION

The present invention relates to inflammation within the body, and more particularly, to regulating inflammation to treat conditions and diseases associated therewith.

Inflammation has been linked to a variety of conditions and diseases that affect the body. For example, inflammation within joints is known to worsen the symptoms of and structural deformities caused by arthritis and rheumatoid diseases, such as bursitis, tendonitis, myositis and osteoarthritis, as well as bone and joint destructive diseases, such as osteoporosis.

Inflammation also is known to contribute to a variety of cardiovascular and metabolic disease processes, such as atherosclerosis, thrombosis, and insulin resistance associated with obesity. Atherosclerosis may increase the chances of stroke and myocardial infarction and insulin resistance may lead to diabetes.

Inflammation is also thought to contribute to the development of neurological disorders, for example, Alzheimer's disease.

Indeed a large body of research now links inflammation with a wide variety of chronic degenerative diseases. This research has identified certain cells—macrophages—that produce pro-inflammatory chemicals—cytokines—which induce signaling cascades that provide an inflammatory response. These cytokines play a role in inflammatory reaction in response to foreign and infectious agents, traumatic or chronic injury, and abnormal chemical or physical stresses.

Accordingly, treatments have been developed to regulate the release of inflammatory cytokines, or the signaling of inflammatory cytokines, specifically the interleukin-1 (IL-1) cytokine from macrophages. For example, U.S. Pat. No. 5,635,478 to Vignery discloses the use of calcitonin gene related peptide (CGRP) to regulate IL-1 release, and thereby treat rheumatoid arthritis. Although highly specific CGRP is effective at regulating IL-1, its use is cost prohibitive and presently it is undetermined whether this compound has a toxic effect with prolonged use.

SUMMARY OF THE INVENTION

The aforementioned problems are overcome in the present invention which provides a composition that regulates interleukin cytokines and/or regulates a physiological response caused by interleukin cytokines. This regulation is effective in controlling an immune response and/or an inflammatory condition. In one aspect, the composition can comprise rosehips and at least one of blackberry, blueberry and elderberry. In another aspect, the composition can comprise rosehips and krill oil. In yet another aspect, the composition can comprise rosehips, blackberry, blueberry, elderberry and krill oil. In a further aspect, the composition can comprise rosehips, resveratrol and *Aframomum melegueta*. In an even further aspect, the composition can comprise rosehips, resveratrol and astaxanthin.

In a fourth aspect, the composition can comprise at least one ingredient chosen from rosehips, blueberry, blackberry, elderberry, cranberry, rosemary, clove, feverfew, nettle root, artichoke, reishi mushroom, olive extract, green tea extract (*epigallocatechin gallate*), grape seed extract, resveratrol, *Aframomum melegueta, boswellia serrata* extract, *boswellia forte*, ipriflavone, tocotrienols, evening primrose oil, INM-176, borage oil, krill oil, at least one type of xanthophyll (e.g., astaxanthin), green coffee extract (chlorogenic acid), and ferulic acid. In a more specific aspect, the composition can comprise rosehips, nettle root, olive extract and artichoke. In yet another specific aspect, the composition can comprise rose hips, resveratrol and astaxanthin.

In a fifth aspect, the invention can provide methods for controlling an immune response and/or an inflammatory condition in a subject, the method comprising administering to the subject an effective amount of the composition of the invention to control the immune response and/or the inflammatory condition. In a specific aspect, the composition can inhibit the function of an immunomodulatory or pro-inflammatory cell, for example, a macrophage and/or a leukocyte. In a more specific aspect, the composition can inhibit the expression of the genes that produce interleukin cytokines, for example, by preventing the genetic transcription of those genes. In an even more specific aspect, the composition can inhibit the interleukin cytokine inflammation response mechanism. In these aspects, the composition can reduce and/or eliminate pro-immunomodulatory and/or pro-inflammatory responses in skeletal mass, joints, muscle, tissue, arteries, veins, capillaries, and other organs, systems and/or cells.

In a sixth aspect, the invention can provide a method of regulating and/or controlling the function of immune cells, such as macrophages, leukocytes and lymphocytes, by administering an effective amount of the composition to a subject.

In another aspect, the invention can provide a method for regulating cytokine release, also referred to as secretion, from cells in a subject by administering to a subject a cytokine inhibiting amount of the composition.

In yet another aspect, the invention can provide a method that inhibits the response of cells to an interleukin cytokine by administering to a subject an effective amount of the composition of the invention. In a specific aspect, this administration can modulate the production of inflammation biomarkers, for example, C reactive protein, which is a biomarker produced by the liver that is indicative of excessive inflammation in the body.

In a ninth aspect, the invention can provide a method for treating a disease or abnormal condition caused by inflammation by administering a therapeutically effective amount of the composition. In a specific aspect, the disease or abnormal condition includes at least one of a cardiovascular disease or condition, thrombosis, a metabolic condition related to insulin resistance and obesity, a traumatic injury, arthritis, osteoporosis, and Alzheimer's disease. In a more specific aspect, the method can include administering the composition to a subject having an inflammatory condition to relieve or eliminate pain, tenderness, infection and/or discomfort following traumatic injuries, surgery or other events that may cause inflammation.

The present invention provides a composition and related methods for treating a variety of immunomodulatory- and inflammation-based conditions, symptoms and diseases. Because the ingredients used are readily available and relatively inexpensive, the present invention provides a simple and cost-effective solution for treating a variety of inflammation-caused ailments and conditions. Furthermore, because the ingredients are relatively stable, many can be mixed with other materials and provided in a multipurpose supplement or food product.

These and other objects, advantages and features of the invention will be more readily understood and appreciated by reference to the drawings and the detailed description of the invention.

DETAILED DESCRIPTION OF THE INVENTION

I. The Composition

Figure 1:
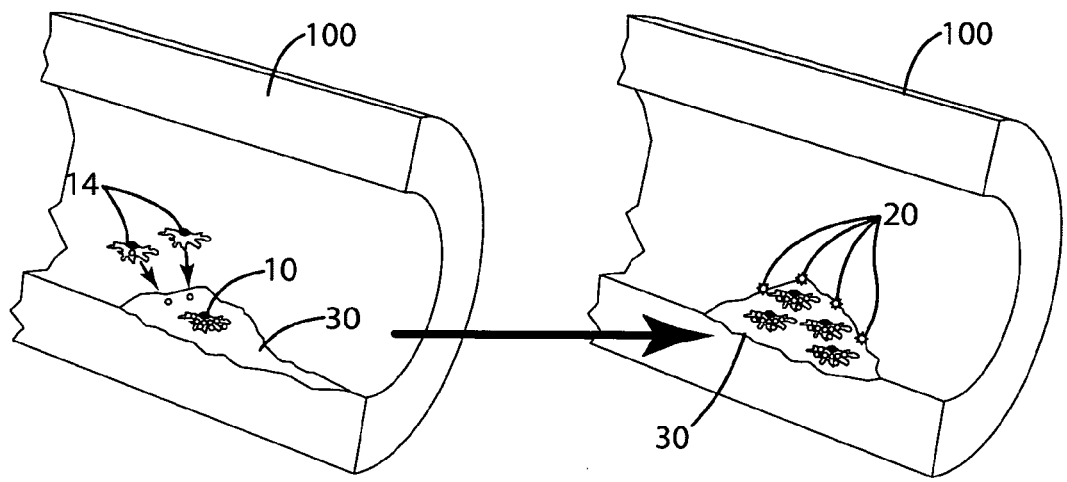
FIG. 1 is a sectional view of a blood vessel of a subject having atherosclerotic plaque development before being treated with the composition of the present invention in Example 3.

A composition of the invention can include one or more ingredients chosen from rosehips, blueberry, blackberry, elderberry, cranberry, rosemary, clove, feverfew, nettle root, artichoke, reishi mushroom, olive extract, green tea extract (*epigallocatechin gallate*), grape seed extract, resveratrol, *Aframomum melegueta, boswellia serrata* extract, *boswellia forte*, ipriflavone, tocotrienols, evening primrose oil, INM-176, borage oil, krill oil, at least one type of xanthophyll (e.g., astaxanthin), green coffee extract (chlorogenic acid), and ferulic acid. Specifically, a composition of the invention can include rosehips and at least one of blackberry, blueberry, elderberry and krill oil. A composition also can include rosehips, resveratrol and *Aframomum melegueta*. Another composition can include rosehips, resveratrol and astaxanthin. The composition can be administered in any of the dosages recited herein to inhibit cytokine expression, production, reception, secretion and/or release, as well as inhibit the cytokine response, thereby reducing or eliminating an immunomodulatory and/or inflammatory response.

Acceptable dosages of the ingredients that may be effective at modulating cytokines, for example, regulating the production, reception, secretion and/or release of exemplary cytokines, such as IL-1 and/or IL-6, are presented in Table I below. Each dosage in Table I is an estimated effective daily dosage in milligrams. Furthermore, all the dosages in Table I are presented in ranges of from about the recited lower limit to about the upper limit. For example, the nettle Dosage A recites "250-2500", which represents a dosage of about 250 to about 2500 milligrams of nettle per day.

TABLE I

Acceptable Dosages for Ingredients to Modulate Cytokines

| Ingredient | Dosage A | Dosage B |
|---|---|---|
| Nettle extract | 250-2500 | 500-1250 |
| Artichoke | 150-1500 | 300-750 |
| Feverfew | 50-500 | 100-250 |
| Reishi mushroom | 300-3000 | 600-1500 |
| Olive extract | 300-3000 | 600-1500 |
| Green tea extract | 150-1500 | 300-750 |
| Grape seed extract | 100-1000 | 200-500 |
| *Aframomum melegueta* extract | 150-1500 | 300-750 |
| *Boswellia serrata* extract | 350-3500 | 700-1750 |

TABLE I-continued

Acceptable Dosages for Ingredients to Modulate Cytokines

| Ingredient | Dosage A | Dosage B |
|---|---|---|
| Ipriflavone | 100-1000 | 200-500 |
| Tocotrienols | 50-500 | 100-250 |
| Evening primrose oil | 500-5000 | 1000-2500 |
| INM-176 | 100-1000 | 200-500 |
| Borage Oil | 500-5000 | 1000-2500 |
| Krill Oil | 300-3000 | 600-1500 |
| Green coffee extract (chlorgenic acid) | 100-1000 | 200-500 |
| Ferulic acid | 100-1000 | 200-500 |
| Rosehips | 50-500 | 500-5000 |
| Blackberry powder | 100-1000 | 200-500 |
| Blueberry powder | 200-2000 | 300-1500 |
| Cranberry extract | 100-1000 | 200-500 |
| Rosemary extract | 100-1000 | 200-500 |
| Clove extract | 100-1000 | 200-500 |
| Resveratrol | 100-1000 | 200-500 |
| Elderberry extract | 400-4000 | 700-2500 |

The ingredients identified above in Table I are readily commercially available. Depending on the application and/or the supplier, the ingredient may be an extract of a specific potency, a pure ingredient, an ingredient mixed with excipients, and in a variety of physical forms, e.g., liquid or powder. The ingredient identified is INM-176 is a compound of unknown composition available from Scigenic Company, Ltd. of Seoul, Korea.

More particularly, the composition can include one or more than one rosehip ingredient. Examples of rosehip ingredients include, without limitation, dried rosehips, rosehip oil, and rosehip extracts. A rosehip ingredient can be obtained from any of the multiple species of plants that belong to the *Rosa* family, for example *Rosa canina*. Moreover, rosehips can include the fruit, petals and/or seeds of the *Rosa* plants.

Any method can be used to prepare a rosehips ingredient. As an example, conventional harvesting and drying methods can be used to prepare dried rosehips. Rosehip oil can be produced with standard methods and processed with cellulose for tableting or powdered compositions. In addition, rosehips can be obtained commercially from MB North America of Torrance, Calif.

A composition of the invention can contain one or more than one rosehips ingredient. For example, a dietary supplement can contain dried rosehips as well as rosehips extract. In addition, a composition can contain any amount of a rosehips component. For example, at least about 1 percent (e.g., at least about 2, 3, 4, 5, 10, 15, 20, 25, 30, 35, 40, 50, 60, 70, 80, or 90 percent) of a dietary supplement can be a rosehips ingredient. Typically, a composition contains between about 500 mg and about 5000 mg of a rosehips ingredient.

Even more particularly, the composition can include one or more than one blackberry ingredient. Examples of blackberry ingredients include, without limitation, dried blackberry, blackberry powder, and blackberry extracts. A blackberry ingredient can be obtained from any of the multiple species of plants that belong to the *Rubus* family, for example *Rubus fruticosus*.

Any method can be used to prepare a blackberry ingredient. As an example, conventional harvesting, drying and powdering methods can be used to prepare blackberry powder. In addition, blackberry can be obtained commercially from Van Drunen Farms Futureceuticals of Santa Rosa, Calif.

A composition of the invention can contain one or more than one blackberry ingredient. For example, a dietary supplement can contain blackberry powder as well as blackberry extract. In addition, a composition can contain any amount of a blackberry component. For example, at least about 1 percent (e.g., at least about 2, 3, 4, 5, 10, 15, 20, 25, 30, 35, 40, 50, 60, 70, 80, or 90 percent) of a dietary supplement can be a blackberry ingredient. Typically, a composition contains between about 100 mg and about 1000 mg of a blackberry ingredient.

Further particularly, the composition can include one or more than one blueberry ingredient. Examples of blueberry ingredients include, without limitation, dried blueberry, blueberry powder, and blueberry extracts. A blueberry ingredient can be obtained from any of the multiple species of plants that belong to the *Vaccinium* family, for example, *Vaccinium corymbosum*.

Any method can be used to prepare a blueberry ingredient. As an example, conventional harvesting, drying and powdering methods can be used to prepare blueberry powder. In addition, blueberry can be obtained commercially from Van Drunen Farms Futureceuticals of Santa Rosa, Calif.

A composition of the invention can contain one or more than one blueberry ingredient. For example, a dietary supplement can contain blueberry powder as well as blueberry extract. In addition, a composition can contain any amount of a blueberry component. For example, at least about 1 percent (e.g., at least about 2, 3, 4, 5, 10, 15, 20, 25, 30, 35, 40, 50, 60, 70, 80, or 90 percent) of a dietary supplement can be a blueberry ingredient. Typically, a composition contains between about 200 mg and about 2000 mg of a blueberry ingredient.

Even more particularly, the composition can include one or more than one elderberry ingredient. Examples of elderberry ingredients include, without limitation, elderberry extracts, dried elderberry and elderberry powder. An elderberry ingredient an be obtained from any of the multiple species of plants that belong to the *Sambucus* family, for example, *Sambucus canadensis*.

Any method can be used to prepare an elderberry ingredient. As an example, conventional extraction techniques can be used to prepare an elderberry extract. In addition, elderberry can be obtained commercially from Artemis International of Fort Wayne, Ind.

A composition of the invention can contain one or more than one elderberry ingredient. For example, a dietary supplement can contain elderberry powder as well as elderberry extract. In addition, a composition can contain any amount of an elderberry component. For example, at least about 1 percent (e.g., at least about 2, 3, 4, 5, 10, 15, 20, 25, 30, 35, 40, 50, 60, 70, 80, or 90 percent) of a dietary supplement can be an elderberry ingredient. Typically, a composition contains between about 400 mg and about 4000 mg of an elderberry ingredient.

Furthermore, the composition can include *Aframomum melegueta*. Examples of *Aframomum melegueta* ingredients include, without limitation, pulverized *Aframomum melegueta* seeds, *Aframomum melegueta* powder, and *Aframomum melegueta* extracts.

Any method can be used to prepare a *Aframomum melegueta* ingredient. As an example, conventional harvesting, drying and extracting methods can be used to prepare *Aframomum melegueta* extracts. In addition, *Aframomum melegueta* can be obtained commercially from Frontier Natural Products Cooperative of Norway, Iowa.

A composition of the invention can contain one or more than one *Aframomum melegueta* ingredient. For example, a dietary supplement can contain *Aframomum melegueta* powder as well as *Aframomum melegueta* extract. In addition, a composition can contain any amount of a *Aframomum melegueta* component. For example, at least about 1 percent (e.g., at least about 2, 3, 4, 5, 10, 15, 20, 25, 30, 35, 40, 50, 60, 70, 80, or 90 percent) of a dietary supplement can be a *Aframomum melegueta* ingredient. Typically, a composition contains between about 500 mg and about 1500 mg of a *Aframomum melegueta* ingredient.

A composition of the invention can include krill oil. Krill oil can be obtained from any member of the *Euphausia* family, for example *Euphausia superba*. Conventional oil producing techniques can be used to obtain the krill oil. In addition, krill oil can be obtained commercially from Neptune Technologies and Bioresources of Quebec, Canada.

A composition can contain any amount of krill oil. For example, at least about 1 percent (e.g., at least about 2, 3, 4, 5, 10, 15, 20, 25, 30, 35, 40, 50, 60, 70, 80, or 90 percent) of a dietary supplement can be a krill oil. Typically, a composition contains between about 300 mg and about 3000 mg of a krill oil ingredient.

Where the composition includes resveratrol, the resveratrol can be obtained from an extract of grape skin or other grape components. Resveratrol can be present in the composition in one or more different forms, for example, extract form and powder form. Resveratrol can be obtained commercially from Charles Bowman & Co. of Holland, Mich.

A composition can contain any amount of a resveratrol component. For example, at least about 1 percent (e.g., at least about 2, 3, 4, 5, 10, 15, 20, 25, 30, 35, 40, 50, 60, 70, 80, or 90 percent) of a dietary supplement can be a resveratrol. Typically, a composition contains between about 100 mg and about 1000 mg of a resveratrol ingredient.

Where the composition includes at least one type of xanthophyll, the xanthophyll can be astaxanthin. Astaxanthin can be obtained from natural sources or synthesized. For example, astaxanthin can be obtained from algae, fingi and/or crustaceans. One type of astaxanthin can be obtained commercially from Cyanotech Corporation of Kailua-Kona, Hi.

A composition can contain any amount of an astaxanthin ingredient. For example, at least about 1 percent (e.g., at least about 2, 3, 4, 5, 10, 15, 20, 25, 30, 35, 40, 50, 60, 70, 80, or 90 percent) of a dietary supplement can be astaxanthin. Typically, a composition contains between about 0.5 mg and about 50 mg of an astaxanthin ingredient.

The composition can include one or more pharmaceutically acceptable excipients, for example, croscarmellose sodium, maltodextrin, silicified microcrystalline cellulose, silicon dioxide, stearic acid, hydroxyl propyl methyl cellulose (HPMC), lactose, glucose, sucrose, corn starch, potato starch, cellulose acetate, ethyl cellulose and the like. Diluents and other additives such as one or more pharmaceutically acceptable binding agents, fillers, supports, thickening agents, taste-improving agents, coloring agents, preservatives, proteins, anti-microbials, chelating agents, inert gases, stabilizers, regulators, emulsifiers or mixtures thereof, can be used depending on the form of the composition employed.

The ingredients of the composition can be processed into forms having varying delivery systems. For example, the ingredients can be processed and included in capsules, tablets, gel tabs, lozenges, strips, granules, powders, concentrates, solutions, lotions, creams or suspensions. The ingredients can also be administered into the respiratory tract, e.g. in the treatment of asthma, anaphylactic or and other acute shock conditions via a spray, mist or aerosol. The ingredients can may be formulated, individually or in combination, with other foods to provide pre-measured nutritional supplements, supplemented foods, for example, single serving bars. In one example, the composition can include one ingredient administered in tablet form, and another composition administered in capsule form. More generally, the composition can be formulated for a variety of administration routes, for example, intravenously, intramuscularly, subcutaneously, nasally, sublingually, intrathecally, topically or intradermally.

The dosages of the composition may be administered in increments determined by the disease or condition being treated. For example, in the treatment of arthritis, the composition may be administered in multiple successive dosages, spaced as frequently as about 6 to about 12 hours apart, and as long as about 2 weeks apart. Daily dosages may be administered for a period to obtain symptomatic relief from inflammatory tenderness, swelling and pain. The dosages may be adjusted to maintain the relief from these symptoms. Treatment may be a period of weeks or months, or optionally, indefinitely for chronic diseases or conditions.

II. Method of Manufacturing the Composition

An exemplary composition of the invention including rosehips, blackberry powder, blueberry powder and elderberry extract can be manufactured in tablet form according to the following processes. Other administration mediums, such as gel tabs, capsules, liquid and sustained release formulations, etc. can be formulated and prepared according to manufacturing techniques well known in the pharmaceutical industry.

Rosehips, blackberry powder, and blueberry powder in the amounts recited in Dosage 1 in Table II above are added to silicone dioxide and placed in a polybag and blended until uniformly and homogeneously mixed. This resultant blend is placed in a Patterson Kelley (P.K.) 100 blender available from Patterson-Kelley Co., East Stroudsburg, Pa. The following ingredients in the order listed are then passed through a Sweco separator equipped with a 20-mesh screen available from Sweco, Inc. of Florence, Ky. directly into the P.K. 100 blender: dextrose, croscarmellose sodium, and silicified microcrystalline cellulose. The resultant composition is blended in the P.K. 100 blender for 15 minutes.

A vegetable-based stearic acid powder is then passed through the Sweco separator directly into the P.K. 100 blender. The resultant mixture is blended for an additional five minutes. The resulting mixture is discharged into totes or super sacks, compressed, and punched into tablets by conventional apparatus. An acceptable range weight for each individual tablet is from about 250 mg to about 500 mg. The amount of rosehips in each tablet is about 1200 mg, the amount of blackberry is about 165 mg and the amount of blueberry is about 330 mg. Tablets manufactured according to this process can be used in the in vivo testing described herein.

A soft gel capsule of the composition can be manufactured to include krill oil. This capsule can be manufactured using conventional capsule manufacturing techniques. The amount of krill oil in each capsule is about 300 mg. These capsules can be administered alone or in conjunction with the tablets of other ingredients of the composition as part of the in vivo testing described herein.

Other compositions of the invention including either rosehips and blackberry powder, or rosehips and blueberry powder, can be manufactured in tablet form according to the tableting process described above. The amount of rosehips in the rosehips/blackberry tablet is about 300 mg, and the amount of blackberry is about 80 mg. The amount of rosehips in the rosehips/blueberry tablet is about 300 mg, and the amount of blueberry is about 40 mg. Tablets manufactured according to this process can be used in the in vivo testing described herein as desired.

Another composition including rosehips, resveratrol and *Aframomum melegueta* can be manufactured in table form according to the tableting process described above, with about 300 mg rosehips, 10 mg resveratrol and 75 mg *Aframomum melegueta* extract.

Another composition of the invention including rosehips, resveratrol and astaxanthin can be manufactured in table form according to the tableting process described above, with about 300 mg rosehips, 10 mg resveratrol and 1 mg astaxanthin.

Yet another composition of the invention including olive extract, artichoke, nettle root and rosehips can be manufactured in tablet form according to the following process. Olive extract, artichoke, nettle root and rosehips in the amounts recited in Dosage 1 in Table II above are added to silicone dioxide and placed in a polybag and blended until uniformly and homogeneously mixed. This resultant blend is placed in a Patterson Kelley (P.K.) 100 blender available from Patterson-Kelley Co., East Stroudsburg, Pa. The following ingredients in the order listed are then passed through a Sweco separator equipped with a 20-mesh screen available from Sweco, Inc. of Florence, Ky., directly into the P.K. 100 blender: dextrose, croscarmellose sodium, and silicified microcrystalline cellulose. The resultant composition is blended in the P.K. 100 blender for 15 minutes.

A vegetable-based stearic acid powder is then passed through the Sweco separator directly into the P.K. 100 blender. The resultant mixture is blended for an additional five minutes. The resulting mixture is discharged into totes or super sacks, compressed, and punched into tablets by conventional apparatus. An acceptable range weight for each individual tablet is from about 250 mg to about 500 mg.

III. Selection of Ingredients for the Composition

The present invention can include an ingredient screening process for selecting ingredients that are optimal for particular health conditions, and that can be used in the composition as desired. For example, in the case of a nutritional supplement for modulating IL-1, the active ingredients can be selected via a unique screening process. The various factors include biological, commercial, regulatory, and descriptive discriminators. Some preferred discriminators and their weighted values are outlined Table 2. Preferably, the discriminators are assigned a weight based upon business or consumer driven objectives. In Table 2, a weight of 3 means that the discriminator carries heavy weighting or importance in the selection process ("Factor 3 Discriminator"); 2 means that the discriminator carries significant weight, but less than a weight factor of 3 in the selection process ("Factor 2 Discriminator"); and 1 carries the least weight as a discriminator ("Factor 1 Discriminator").

TABLE II

Discriminators for Selecting Cytokine Modulating Ingredients

| Discriminator | Weight |
| --- | --- |
| Performance in IL-1 screening assay (EC <50 ug/ml) | 3 |
| Supply Availability | 3 |
| Cost per kilogram of material | 3 |
| Raw Material Name | 1 |
| Botanical Identity/Parent Extract | 1 |
| Optional and secondary material and suppliers | 2 |
| Potential for exclusivity | 2 |
| Vertical integration possibility | 2 |
| Aqueous versus hydrophobic compatibility | 2 |

TABLE II-continued

Discriminators for Selecting Cytokine Modulating Ingredients

| Discriminator | Weight |
|---|---|
| Known active ingredients/Mechanism of action | 2 |
| Fractional bioavailability* | 2 |
| Efficacious daily dose based upon in vitro EC 50 mg | 2 |
| Efficacious daily dose based upon literature (mg) | 2 |
| Estimated raw material cost based upon bioassay EC 50 and bioavailability (cost per month) | 2 |
| Estimated raw material cost based upon literature efficacy (cost per month) | 2 |
| Safety/Toxicity status | 3 |
| Technical/Regulatory acceptance in market country | 3 |
| Representation in the source company's products and in the general marketplace | 2 |
| Intellectual property risks | 2 |

*Fractional bioavailability is the percentage of the active compounds in an orally ingested ingredient (expressed as a fraction) that is absorbed into the body, and is generally available to body tissues via the circulation. For example, a fractional availability of 0.10 indicates that 10% of an orally ingested ingredient's actives are absorbed from the intestinal tract and are (for some period of time) transported in the circulation.

In the above example, the primary objective is to find an effective and commercially successful IL-1 modulator for human use. Selection of the best candidates is accomplished by summing the discriminator weights for each candidate and comparing total weighted score. Thus, performance of an active ingredient in modulating IL-1 is relevant, as is the expense to obtain the particular ingredient and the availability of the ingredient. Other factors relevant to commercial success are the ingredient's toxicity and safety as well as the technical and regulatory acceptance of the ingredient in the market where the composition will be sold. There may be cases where some ingredients do not meet one Factor 3 Discriminator, and the one Factor 3 Discriminator is different for each ingredient. In these cases, Factor 3 Discriminators are assigned weights and Factor 2 and Factor 1 Discriminators are also considered in the selection process.

In addition to the above ingredient screening process, the therapeutic composition or ingredient is preferably subjected to an ex vivo clinical evaluation to confirm the biological properties and effects. In particular, the subject consumes the therapeutic composition or ingredient. Serial blood samples are obtained from the subject before and following consumption over a time period when the ingredient's active components are likely to be absorbed by and transported within the circulatory system of the body, which is about 6 hours for most chemicals. These blood samples are added to an in vitro bioassay system which has an assay or test readout that is sensitive to changes in the physiology of the system of interest. The results of this test, referred to as an ex vivo test, are compared to the results from the in vitro clinical. The closer the results of the in vitro and ex vivo evaluations the greater the likelihood that the therapeutic will have desired effect within the body.

IV. Cytokine Inhibitory Potential Evaluation

The ingredients of the composition can modulate cytokines via at least two different biological mechanisms. In a first mechanism, the ingredients can inhibit the production, i.e., synthesis, of interleukin cytokines. In this mechanism, it is believed that the ingredients prevent the mRNA transcription of the genes that code for the production of the interleukin cytokines. Therefore, with genetic transcription blocked, the cytokines can not be synthesized by or in the body. In a second mechanism, the ingredients can inhibit the cascading response of chemicals and cells in the body to the interleukin cytokines. More particularly, the ingredients can prevent the production of—among other compounds—acute phase proteins, for example, C reactive protein (CRP). CRP is synthesized in the human liver by hepatocytes in response to interleukin cytokines, e.g., IL-1 and IL-6, under traumatic and/or inflammatory conditions. The ingredients can affect the response mechanism of cells, for example, liver cells, to interleukin cytokines so that those cells reduce or stop production of CRP.

In the following examples, the interleukin cytokine modulating potential, in both inhibiting the synthesis of cytokines and inhibiting the response caused by cytokine, of the various listed ingredients was measured and the results of each exposure was reported and evaluated.

For this evaluation, white blood cells were dosed with varying concentrations of the ingredients. An inflammatory stimulus, lipopolysaccharide (LPS), was then added to the ingredient-plus-cell culture, as well as untreated control samples of white blood cells. The production of the IL-1 cytokine of both the ingredient-treated cells and the untreated cells was compared to extrapolate the concentration of the ingredient that causes a 50% change in the concentration of IL-1 produced by the cells.

These examples are presented for purposes of further illustrating and explaining the present invention and is not to be taken as limiting in any regard. Unless otherwise indicated, all temperature measurements are in degree Celsius.

Example 1

To perform the evaluation of inhibiting interleukin synthesis of this example, human white blood cells, specifically THP-1 cells obtained from ATCC of Manassas, Va., were grown under conditions recommended by ATCC in a humidified 37° C. incubator, which was supplied with 5% carbon dioxide. To test the IL-1 inhibitory potential of various compounds, multiple groups of THP-1 cells were plated in 96 well plates. Specifically, $5 \times 10^5$ THP-1 cells were plated in RPMI 1640 supplement with 10% fetal bovine serum and antibiotics, such as penicillin and streptomycin. With these cell samples plated, they were then dosed.

In dosing, each of the ingredients was administered to the plated THP-1 cells in varying doses, specifically, 100 ug/ml, 10 ug/ml, 1 ug/ml and 0 ug/ml. For example, in one plate of cells, 100 micrograms per milliliter of nettle root extract were administered, in another, 10 micrograms per milliliter were administered, in another 1 microgram per milliliter were administered, and in yet another no nettle root was administered. With the plated cells treated with the respective ingredients, the THP-1 cells, now dosed with the ingredient, were returned to the incubator and incubated for 4 hours under the same conditions.

Thereafter, a known inflammatory stimulator, LPS was added to each well plate to a final concentration of 100 nanograms/ml. The LPS treated cultures were returned to the incubator for an additional 16 hours. The cultures were then centrifuged at 1000 Gs for about 5 minutes to obtain a supernatant. The supernatants were then labeled and organized for IL-1 detection.

To detect secreted IL-1 in the different dosed supernatants and therefore evaluate the IL-1 secretion inhibitory potential of each dosage of each ingredient, each supernatant was tested for presence of IL-1 according to a conventional IL-1 testing protocol provided by the supplier of the tests, Biosource International of Camarillo, Calif. The specific protocol is provided in the reference, *Protocol Booklet, Human IL-1*, (2001), available from Biosource International, which is hereby incorporated by reference.

In general accordance with the protocol, 50 microliters of each supernatant sample was added to well of the anti-IL-1 coated plates, which were incubated at room temperature for 2 hours. Likewise, calibration standards designed to establish known amounts of IL-1 were added to the designated wells of anti-IL-1 antibody coated plates and incubated at room temperature for 2 hours.

Thereafter, the liquids from each of the wells were removed and the coated plate was washed 3 times in a wash buffer. After the third wash, 100 microliters of enzyme (horseradish peroxidase) conjugated anti-IL-1 antibody was added to each wells of the coated plates and incubated at room temperature for 30 minutes. The plate was washed again as before and 100 microliters of substrate solution, (TMB), was added to each wells to indicate amount of the IL-1 produced as a result of adding the LPS inflammation stimulator in presence or absence of the mentioned ingredients. Thereafter, 100 microliters of a stop solution, such as hydrochloric or sulfuric acid, was added to stop the reaction. The reaction of the substrate solution (TMB) and the horseradish peroxidase conjugated to the anti-IL-1 antibody produces a colored product with specific spectral absorbance at wavelength of 450 nm. Hence the amount of IL-1 present is determined by measuring the amount of absorbance at 450 nm resulting from the amount of bound enzyme conjugated anti-IL-1 antibody depending on the amount of IL-1 present.

The calibration standard samples were subjected to the same protocol as the supernatant samples to determine the IL-1 present in those calibration samples. The optical density of the calibration standard samples was tested to establish a known absorbance of IL-1 at varying levels, for example, 1500 to 50, 125, 62.5, 31.2 and 0 picograms per milliliter in calibration dilutent. The optical density of the standard calibration samples were then plotted to determine a standardized IL-1 absorbance calibration curve.

For each sample supernatant tested and optically measured, the absorbance was plotted against the standard IL-1 absorbance calibration curve to determine the amount of IL-1 present in the sample supernatant.

Based on the amount of IL-1 present in the sample supernatant, the results of the IL-1 inhibitory potential of the various ingredients was recorded as noted in Table III below. As indicated there, the results are reported in EC50 values, which is a commonly accepted measurement of effective dosages. Generally speaking, the EC50 is the concentration of ingredients required to cause 50% change in IL-1 concentrations when compared to control samples.

TABLE III

Results of IL-1 Assays in Example 1

| Ingredient | EC 50 in ug/ml (50% Effective Dose in vitro) |
| --- | --- |
| Epigallocatechin gallate | <1 |
| Grape seed extract | <1 |
| Grape seed extract | <1 |
| Ipriflavone | <1 |
| Nettle root extract | <1 |
| Rosehips | <1 |
| Tocotrienols | 1-10 |
| Borage oil | 1-10 |
| Evening primrose oil | 1-10 |
| Green coffee extract | 1-10 |
| INM-176 | 1-10 |
| *Boswellia serreta* | <1-10 |
| *Boswellia forte* | 1-10 |
| Nettle root extract | 1-10 |
| Olive extract | 1-10 |
| Krill oil | 1-10 |
| Reishi mushroom | 1-10 |
| *Afromomum melegueta* extract | 1-10 |
| Feverfew | 1-10 |
| Artichoke | 1-10 |
| Ferulic acid | 10 |

The results of the testing in Table III illustrate the effectiveness of these ingredients in reducing and/or inhibiting the secretion or production of cytokines, for example, IL-1.

Example 2

In this example, other ingredients that can be included in the composition of the invention were tested to (a) evaluate the effectiveness of these ingredients in reducing and/or inhibiting the secretion or production of cytokines, for example, IL-1; (b) evaluate interaction of the other ingredients with optional primary ingredients (rosehips, artichoke extract, olive extracts and nettle root); and (c) evaluate the effects of the other ingredients on interleukin cytokine, e.g., IL-1, response in hepatocytes by measuring the C reactive protein (CRP) secretion by hepatocytes.

Specifically, the release of IL-1β from the THP-1 cells after exposure to lipopolysaccharide (LPS) with or without pre-treatment in varying doses of the other ingredients, or a combination of those other ingredients with optional primary ingredients, was measured to evaluate the effects of the other ingredients on monocyte IL-1β secretion. Hepatocytes' response to IL-1 was evaluated by measuring CRP in the culture supernatant after exposure to IL-1 and IL-6 with or without pre-treatment with varying doses of the other ingredients.

The other ingredients tested were: blackberry extract, blueberry extract, cranberry extract, rosemary extract, clove extract and resveratrol. Table IV, demonstrates the results of these other ingredients for dose specific inhibition of IL-1β secretion upon activation via LPS in absence or presence of additional 4 primary ingredients at low dose. The methodology used to test the inhibition of IL-1β secretion is the same as that in Example 1 for the ingredients tested there. Of the ingredients tested in this Example 2, rosemary extract, blueberry extract, elderberry extract, cranberry extract had IL-1 modulatory effects at relatively low dose (ranging from 20-70 ug/ml).

Interference of the other ingredients with the IL-1 modulatory effects of the listed optional primary ingredients was tested by comparing the optional primary ingredients IL-1 secretion inhibitory effects, for example those shown in Table III, with the IL-1 secretion inhibitory effects of those primary ingredients in combination with the other ingredients listed in Table IV. For example, the presence of blackberry did not alter the IL-1 modulating effect of rosehips as illustrated by the absence of the characteristic inhibitory activity. None of the other ingredients showed interference with the optional primary ingredients, but some showed synergistic effects (blueberry extract showed synergistic effect with rosehips and nettle root, and elderberry extract with artichoke extract and nettle root). In Table IV, a "−" indicates no interference or no synergy, and a "+" indicates interference or synergy, respectively as shown.

The IL-1 response effects were evaluated in hepatocytes by measuring the secretion of CRP when the hepatocytes were exposed to IL-1β and IL-6 with or without pre-treatment with varying doses of the other ingredients. CRP secretion was chosen because, as noted above, CRP is a significant acute-phase protein in humans; its plasma concentration increases more than 1000-fold during severe trauma and/or inflammation; and CRP is expressed, e.g., synthesized or secreted, in hepatocytes in response to IL-1 and IL-6 under inflammatory conditions. CRP acts as a biomarker for interleukin cytokines, and it is efficient to measure this biomarker rather than the cytokines themselves because cytokine levels in the blood frequently do not accurately reflect the actual amount of the cytokines in the body. Thus, by measuring CRP secreted by the hepatocytes, the degree of cells' response to IL-1 and/or IL-6 is able to be determined.

To perform the evaluation of this example, human primarily isolated hepatocyte cells, obtained from In Vitro Technology of Baltimore, Md., were restored under the conditions recommended by In Vitro Technology in a humidified 37° C. incubator, which was supplied with 5% carbon dioxide. To test the CRP response potential of various compounds, multiple groups of hepatocytes were plated in 96 well plates. Specifically, $1 \times 10^4$ cells were plated in hepatocyte media supplement with 10% fetal bovine serum which were then exposed with varying doses, specifically, 100 ug/ml, 10 ug/ml, 1 ug/ml and 0 ug/ml of test ingredients. For example: in one plate of cells, 100 micrograms per milliliter of blackberry extract were administered; in another, 10 micrograms per milliliter were administered; in another 1 microgram per milliliter were administered; and in yet another no nettle root was administered. With the plated cells treated with the respective ingredients, the hepatocytes, now dosed with the ingredient, were returned to the incubator and incubated for 4 hours under the same conditions.

Thereafter, a known CRP inducer, such as IL-1 and IL-6 was added to each well plate to a final concentration of 1 nanograms/ml. The LPS treated cultures were returned to the incubator for an additional 16 hours. After the incubation, the supernatants were then labeled and organized for CRP detection.

To detect secreted CRP in the different dosed supernatants and therefore evaluate the CRP secretion inhibitory potential of each dosage of each ingredient, each supernatant was tested for presence of CRP according to a conventional CRP testing protocol provided by the supplier of the tests, Life Diagnostics, Inc. of West Chester, Pa. The specific protocol is provided in the reference, *High Sensitivity C-Reactive Protein Enzyme Immunoassay Test Kit*, (2003), available from Life Diagnostics, Inc., which is hereby incorporated by reference.

In general accordance with the protocol, 10 microliters of each supernatant sample was added to well of the anti-CRP antibody coated plates along with 100 ul of second antibodies against CRP conjugated to the horse radish peroxidase, which were incubated at room temperature for 45 minutes. Likewise, calibration standards designed to establish known amounts of CRP were added to the designated wells of anti-CRP antibody coated plates along with the second anti-CRP antibodies conjugated to the HRP and incubated at room temperature for 45 minutes.

Thereafter, the liquids from each of the wells were removed and the coated plate was washed 3 times in a wash buffer. After the third wash, 100 microliters of substrate solution, (TMB), was added to each wells to indicate amount of the CRP produced as a result of adding the IL-1 and IL-6, CRP inducer in presence or absence of the mentioned ingredients. Thereafter, 100 microliters of a stop solution, such as hydrochloric or sulfuric acid, was added to stop the reaction. The reaction of the substrate solution (TMB) and the horseradish peroxidase conjugated to the anti-CRP antibody produces a colored product with specific spectral absorbance at wavelength of 450 nm. Hence the amount of CRP present is determined by measuring the amount of absorbance at 450 nm resulting from the amount of bound enzyme conjugated anti-CRP antibody depending on the amount of CRP present.

The calibration standard samples were subjected to the same protocol as the supernatant samples to determine the CRP present in those calibration samples. The optical density of the calibration standard samples was tested to establish a known absorbance of CRP at varying levels, for example, 0, 0.005, 0.01, 0.025, 0.05, and 0.1 microgram per milliliter in calibration diluent. The optical density of the standard calibration samples were then plotted to determine a standardized CRP absorbance calibration curve.

For each sample supernatant tested and optically measured, the absorbance was plotted against the standard CRP absorbance calibration curve to determine the amount of CRP present in the sample supernatant.

Based on the amount of CRP present in the sample supernatant, the results of the CRP inhibitory potential of the various ingredients was recorded as noted in Table III below. As indicated there, the results are reported in EC50 values, which is a commonly accepted measurement of effective dosages. Generally speaking, the EC50 is the concentration of ingredients required to cause 50% change in CRP concentrations (e.g., a reduction in CRP or an inhibition of CRP synthesis) when compared to control samples.

When IL-1 response effects were evaluated in hepatocytes in the form of CRP secretion, blackberry extract, cranberry extract and resveratrol had potent activity with EC50 of 1-10 ug/ml. Thus, these ingredients were effective at modulating IL-1/IL-6 response, specifically by reducing the synthesis of biomarkers, for example, CRP. Blueberry powder, rosemary extract and elderberry powder also had some activity in modulating IL-1/IL-6 responses. Additional, selected ingredients were tested for dose specific inhibition of CRP secretion upon activation via IL-1 and IL-6 (1 ng/ml each). Of the additional ingredients tested, 10% natural astaxanthin, *Aframomum melegueta* extract (w/o carrier) and Reveravine (resveratrol) showed potent CRP lowering activity with EC50s of about 0.3, 0.6 and 0.8 ug/ml, respectively. Astaxanthin beadlet showed activity with EC50 of slightly over 1 ug/ml.

TABLE IV

Example 2 Results Including EC50 of Other Ingredients In Inhibiting LPS Stimulated IL-1 Secretion, IL-1/IL-6 Stimulated CRP Secretion, and Synergistic or Antagonistic Effects With Optional Primary Ingredients

| Ingredient | IL-1 EC 50 in ug/ml (50% Effective Dose in vitro) | CRP EC 50 in ug/ml (50% Effective Dose in vitro) | Synergy | +/− | Interference | +/− |
|---|---|---|---|---|---|---|
| Blackberry Powder | N/A | 1-10 | Rosehips | | − Rosehips | − |
| | | | Artichoke | | − Artichoke | − |
| | | | Nettle Root | | − Nettle Root | − |
| | | | Olive Extract | | − Olive Extract | − |
| Blueberry Powder | 30-40 | 10-20 | Rosehips | + | Rosehips | − |
| | | | Artichoke | − | Artichoke | − |
| | | | Nettle Root | + | Nettle Root | − |
| | | | Olive Extract | − | Olive Extract | − |

TABLE IV-continued

Example 2 Results Including EC50 of Other Ingredients In
Inhibiting LPS Stimulated IL-1 Secretion, IL-1/IL-6 Stimulated
CRP Secretion, and Synergistic or Antagonistic Effects With
Optional Primary Ingredients

| Ingredient | IL-1 EC 50 in ug/ml (50% Effective Dose in vitro) | CRP EC 50 in ug/ml (50% Effective Dose in vitro) | Synergy | +/− | Interference | +/− |
|---|---|---|---|---|---|---|
| Cranberry Extract | >100 | 1-10 | Rosehips | − | Rosehips | − |
|  |  |  | Artichoke | − | Artichoke | − |
|  |  |  | Nettle Root | − | Nettle Root | − |
|  |  |  | Olive Extract | − | Olive Extract | − |
| Rosemary Extract | 20-30 | 30-40 | Rosehips | − | Rosehips | − |
|  |  |  | Artichoke | − | Artichoke | − |
|  |  |  | Nettle Root | − | Nettle Root | − |
|  |  |  | Olive Extract | − | Olive Extract | − |
| Clove Extract | N/A | N/A | Rosehips | − | Rosehips | − |
|  |  |  | Artichoke | − | Artichoke | − |
|  |  |  | Nettle Root | − | Nettle Root | − |
|  |  |  | Olive Extract | − | Olive Extract | − |
| Resveratrol | N/A | 1-10 | Rosehips | − | Rosehips | − |
|  |  |  | Artichoke | − | Artichoke | − |
|  |  |  | Nettle Root | − | Nettle Root | − |
|  |  |  | Olive Extract | − | Olive Extract | − |
| Elderberry Extract | 60-70 | 30-40 | Rosehips | − | Rosehips | − |
|  |  |  | Artichoke | + | Artichoke | − |
|  |  |  | Nettle Root | + | Nettle Root | − |
|  |  |  | Olive Extract | − | Olive Extract | − |

Example 3

In vivo testing will be conducted on approximately 150-200 human subjects by administering a composition of the invention in daily dosages over a twenty week period. More specifically, the composition will be tested to evaluate (a) the inhibition of IL-1 synthesis in Pattern 1 individuals, and (b) evaluate the inhibition of IL-1 response as measured by CRP levels in Pattern 2 individuals having CRP levels above 3 mg CRP/L blood.

For purposes of this example, Pattern 1 individuals are humans who have of IL-1 genotypes known to possess "normal" or "exaggerated" IL-1 gene expression responses. The exaggerated IL-1 gene expression genotype is defined as the presence of at least one copy of allele 2 at the +3954 locus of the IL-1β gene or two copies of allele 2 at the +4845 locus of the IL-1α gene. In this example, Pattern 2 individuals are humans who have elevated blood levels of inflammation biomarkers, for example, CRP levels of about 3 to about 10 mg/L or more. With this range of CRP, there appears to be a greater opportunity for observing noticeable improvement, i.e., reduction of CRP levels. In other words, it likely will be possible to detect modest decreases in CRP in Pattern 2 subjects.

One composition of the invention that will be administered to fifty test subjects in tablet form daily will include rosehips, blackberry and blueberry, in the daily amounts: 1200 mg rosehips, 165 mg blackberry and 330 mg blueberry.

Another composition of the invention that will be administered to fifty test subjects will include rosehips, blackberry, blueberry and *Aframomum melegueta*, in the daily amounts: 1200 mg rosehips, 165 mg blackberry, 330 mg blueberry and 300 mg *Aframomum melegueta*. These ingredients will be in tablet form.

A further composition of the invention that would be administered to 50 test subjects will include rosehips, *Aframomum melegueta* and resveratrol (e.g., Resveravine, a resveratrol product commercially available from Bio Serae of Bram, France) in the daily amounts 1200 mg rosehips, 150 mg *Aframomum melegueta* and 40 mg resveratrol. These ingredients will be in tablet form.

A placebo, including no ingredients of the composition, will be administered daily in tablet form to fifty subjects.

The first twelve weeks of administering the above compositions and placebo to the respective subjects will be the double blind phase of the testing. During this phase the dosages above will be the loading dose. After the twelfth week, the single blind phase of testing will begin. During this phase, the dosages above may be altered to maintenance dosages, which will be extrapolated from the loading phase data.

In the in vivo testing of this example, blood samples will be taken from the subjects to measure IL-1 and CRP. This blood sampling will be controlled, however, to quantify and minimize intra-individual variability. For example, inflammation biomarkers, such as CRP, and gene expression outcomes, such as the transcription and subsequent synthesis of IL-1, will be measured in multiple, fasting blood samples; and samples from women will be obtained during the same week as those subjects' monthly menstrual cycle. The reason for this is that it has been discovered that high fat meals and menstrual cycles acutely increases inflammation biomarkers. Further, this CRP monitoring protocol suggests taking multiple sampling on different, proximate days.

After administration, the efficacy of the placebo, first and second compositions will be evaluated by ex vivo IL-1 production inhibition (see methods above), in vivo IL-1 gene expression, and blood levels of inflammatory biomarkers, e.g., IL-6, TNF, IL-10, IL-12, Serum Amyloid A, Fibrinogen, ICAM-1, C reactive protein, etc. In vivo IL-1 gene expression will be evaluated by measuring the amount of IL-1 mRNA in subject leukocytes by rtPCR. Evidence of an effective intervention for regulation of the inflammatory process include inhibition of ex vivo IL-1 production, inhibition of in vivo IL-1 gene expression, and decreased levels of one or more inflammatory biomarkers as listed above.

The results of the in vivo testing of this example are expected to illustrate that the composition has the effect of modulating interleukin cytokines by both inhibiting the synthesis of interleukin cytokines and inhibiting the cascading response caused by interleukin cytokines in the subjects. A particular example of this benefit will now be described in connection with a subject having atherosclerotic plaque development exacerbated by inflammation, with reference to FIGS. 1-3.

FIG. 1 illustrates how inflammation and interleukin cytokines contribute to atherosclerotic plaque development. Specifically, mononuclear leukocytes 10 enter artery wall tissue 100, engulf oxidized lipids, recruit additional leukocytes 14 with inflammatory cytokines, e.g., IL-1, stimulate plaque growth 30 via growth factors, which results in stenosis. The cytokines 20 released by the leukocytes within the plaque lead to plaque instability, and can ultimately cause rupture and thrombosis.

Figure 2:
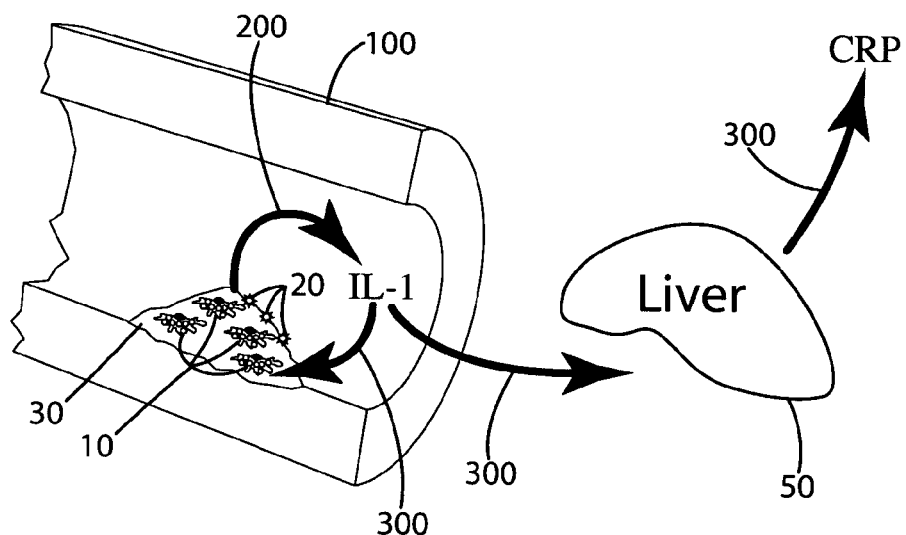
FIG. 2 is a second sectional view of the blood vessel and a liver of a subject that illustrates the effects of interleukin cytokines in atherosclerotic plaque development in Example 3.

In FIG. 2, the synthesis of IL-1 200 and the IL-1 response 300 is shown. Specifically, the leukocytes 10 synthesize the cytokines 20, which in turn stimulate liver 50 production of acute phase proteins, e.g., CRP.

Figure 3:
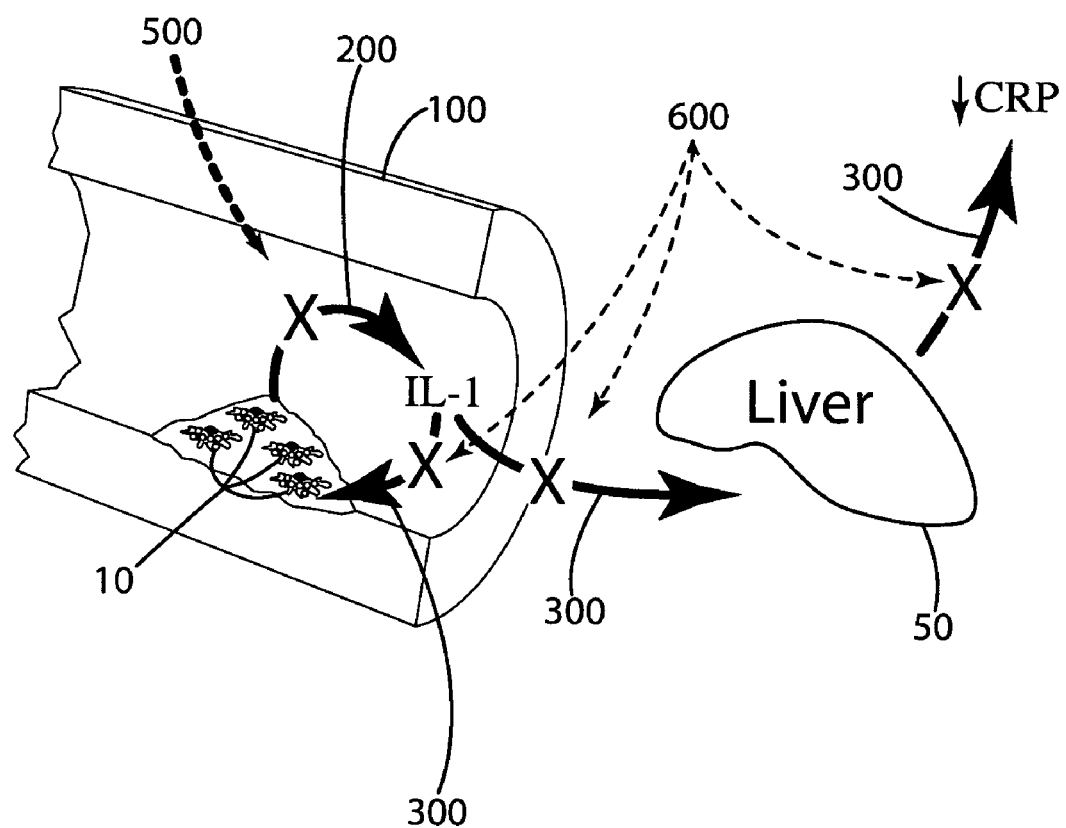
FIG. 3 is a third sectional view of the blood vessel and the liver of a subject that illustrates the effects of the composition on interleukin cytokines in atherosclerotic plaque development in Example 3.

With reference to FIG. 3, the composition of the invention inhibits the production of the cytokines 200 by the leukocytes 10. Specific ingredients 500, e.g., rosehips, blueberry and elderberry, can be targeted to perform this function. The composition of the invention may also inhibit the response 300 of cells and/or the liver 50 to the cytokines by reducing or eliminating the synthesis of CRP. Specific ingredients 600, e.g., blackberry, resveratrol, *Aframomum melegueta* and/or astaxanthin can be targeted to perform this function.

V. Methods of Use

Based on the results of the testing of the ingredients that can be included in the composition of the invention in Examples 1-3 above, it is evident that compositions including these ingredients can be administered to subjects to modulate interleukin cytokines, and specifically to inhibit interleukin cytokine synthesis, decrease C reactive protein synthesis, and/or inhibit the response to interleukin cytokines in the body of the subject.

Given that cytokines, such as IL-1 and IL-6, are key mediators of the inflammatory response in the body, the composition of the invention can be used to modulate the inflammatory response associated with diseases and/or abnormal conditions. For example, the composition may be used to treat arthritis, cardiovascular conditions, osteoporosis, Alzheimer's disease, an inflammatory response to a traumatic injury, or any other abnormal conditions or diseases associated with inflammation or immunomodulatory responses, such as pain and stiffness associated with inflammation.

More specifically, osteoporosis has been linked to abnormally high IL-1 release levels. Therefore, contemplated within this invention is a method for treating osteoporosis by regulating IL-1 through administration of a therapeutically effective amount of the composition of the invention.

Given the connection between inflammation and cardiovascular diseases, such as atherosclerosis and thrombosis, also contemplated within this invention is the treatment of such cardiovascular diseases by administering a therapeutically effective amount of the composition including at least one of the ingredients in the dosages recited above. Additionally, it is believed that the IL-1 regulating composition of the invention may be used to limit or to control an inflammatory response due to surgery, trauma and allergic reactions involving the skin, lungs, eyes, ears, nose, throat, digestive tract, nervous system and the like.

Furthermore, it has been observed that nervous system cells and tissue secrete significant amounts of IL-1 and when stressed under inflammation, and therefore, the composition may be used to treat mental problems, headaches and earaches, as well as debilitating neurological diseases such as Alzheimer's diseases.

The above descriptions are those of the preferred embodiments of the invention. Various alterations and changes can be made without departing from the spirit and broader aspects of the invention as defined in the appended claims, which are to be interpreted in accordance with the principles of patent law including the doctrine of equivalents. Any references to claim elements in the singular, for example, using the articles "a," "an," "the," or "said," is not to be construed as limiting the element to the singular.

The embodiments of the invention in which an exclusive property or privilege is claimed are defined as follows:

1. A composition comprising a combination of dried rosehips (*Rosa canina*) or an extract, oil, or powder of rosehips and a dried blueberry (*Vaccinium*) or an extract or powder of blueberry to provide a daily dosage of about 50-5000 rosehips and about 40-2000 mg blueberry wherein the combination inhibits secretion of an interleukin cytokine in a subject; and wherein the composition further comprises at least one of blackberry (*Rubus*), elderberry (*Sambucus*), resveratrol, and *Aframomum melegueta*.

2. The composition of claim 1, wherein the composition further comprises blackberry to provide a daily dosage of about 100-1000 mg blackberry.

3. The composition of claim 1 or claim 2, wherein the composition further comprises resveratrol.

4. The composition of claim 2, wherein the composition further comprises one or more of the following: elderberry, resveratrol, and *Aframomum melegueta*, and if present to provide a daily dosage of about 200-1000 mg elderberry, about 100-1000 mg resveratrol, and about 150-1500 mg *Aframomum melegueta*.

5. The composition of claim 1, wherein the composition provides a daily dosage of about 1200 mg rosehips and about 164 mg blueberry.

6. The composition of claim 1, wherein the composition provides a daily dosage of about 1200 mg rosehips and about 330 mg blueberry.

7. The composition of claim 6 further comprising blackberry to provide a daily dosage of about 165 mg blackberry.

* * * * *